US011839461B2

(12) United States Patent
Izmirli et al.

(10) Patent No.: US 11,839,461 B2
(45) Date of Patent: Dec. 12, 2023

(54) LOCALIZED MAGNETIC FIELD TRANSMITTER

(71) Applicant: St. Jude Medical International Holding S.á r.l., Luxembourg (LU)

(72) Inventors: Alon Izmirli, Ganot Hadar (IL); Guy Hevel, Zichron Yaakov (IL); Adrian Herscovici, Haifa (IL); Yuval Vaknin, Hanaton (IL); David Jacobs, Naharija (IL)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 142 days.

(21) Appl. No.: 17/350,969

(22) Filed: Jun. 17, 2021

(65) Prior Publication Data

US 2021/0307639 A1 Oct. 7, 2021

Related U.S. Application Data

(63) Continuation of application No. 16/969,551, filed as application No. PCT/IB2019/051090 on Feb. 11, 2019, now Pat. No. 11,071,471.

(60) Provisional application No. 62/630,390, filed on Feb. 14, 2018.

(51) Int. Cl.
| | |
|---|---|
| *A61B 5/06* | (2006.01) |
| *A61B 34/20* | (2016.01) |
| *A61B 5/00* | (2006.01) |
| *G01R 33/30* | (2006.01) |
| *A61B 6/00* | (2006.01) |

(52) U.S. Cl.
CPC ............ *A61B 5/062* (2013.01); *A61B 5/6852* (2013.01); *A61B 34/20* (2016.02); *G01R 33/307* (2013.01); *A61B 6/4441* (2013.01); *A61B 2034/2051* (2016.02)

(58) Field of Classification Search
CPC . A61B 34/20; A61B 2034/2051; A61B 5/062; A61B 5/6852; A61B 6/4441; G01R 33/307
USPC ......................................................... 600/409
See application file for complete search history.

(56) References Cited

U.S. PATENT DOCUMENTS

| | | | |
|---|---|---|---|
| 6,233,476 | B1 | 5/2001 | Strommer et al. |
| 7,197,354 | B2 | 3/2007 | Sobe |
| 7,386,339 | B2 | 6/2008 | Strommer et al. |

(Continued)

FOREIGN PATENT DOCUMENTS

| | | |
|---|---|---|
| CN | 105167787 A | 12/2015 |
| CN | 105813560 A | 7/2016 |

(Continued)

OTHER PUBLICATIONS

Machine Translation of JP2005532878A (Year: 2005).*

(Continued)

*Primary Examiner* — John Denny Li
(74) *Attorney, Agent, or Firm* — Billion & Armitage

(57) ABSTRACT

Aspects of the present disclosure are directed to apparatuses for generating a magnetic field for tracking of a target object. Such an apparatus may include a localized magnetic field transmitter that generates a magnetic field and exhibits minimal X-ray absorption when used in proximity to a fluoroscopic imaging system, for example.

7 Claims, 10 Drawing Sheets

(56) References Cited

U.S. PATENT DOCUMENTS

| | | | |
|---|---|---|---|
| 2003/0052104 A1* | 3/2003 | Matsumoto | C04B 35/185 |
| | | | 219/121.75 |
| 2007/0055142 A1* | 3/2007 | Webler | A61B 5/062 |
| | | | 600/425 |
| 2007/0157828 A1* | 7/2007 | Susel | H01F 41/076 |
| | | | 101/35 |
| 2007/0244388 A1 | 10/2007 | Sato | |
| 2010/0305427 A1 | 12/2010 | Huber et al. | |
| 2016/0287133 A1 | 10/2016 | Eichler et al. | |
| 2017/0007155 A1 | 1/2017 | Gliner | |
| 2017/0007156 A1 | 1/2017 | Govari et al. | |
| 2017/0135602 A1 | 5/2017 | Vaknin et al. | |
| 2017/0188882 A1* | 7/2017 | Foster | H01F 27/2804 |
| 2017/0345754 A1* | 11/2017 | Yun | H01L 23/528 |
| 2018/0256247 A1* | 9/2018 | Govari | A61B 5/6885 |
| 2019/0343422 A1 | 11/2019 | Shlomovitz et al. | |

FOREIGN PATENT DOCUMENTS

| | | | | |
|---|---|---|---|---|
| JP | 10199727 A | | 7/1998 | |
| JP | 2002090176 A | | 3/2002 | |
| JP | 2005532878 A | * | 11/2005 | ............ A61B 5/06 |
| JP | 2009189384 A | | 8/2009 | |
| JP | 2017111871 A | | 6/2017 | |
| WO | WO-2014116961 A1 | * | 7/2014 | ............ A61B 34/20 |

OTHER PUBLICATIONS

"Communication under Rule 71(3) EPC received for European Patent Application No. 21154539.7, dated Dec. 13, 2022", 41 pages.
"Office Action dated Feb. 17, 2023", 2 Pages.

\* cited by examiner

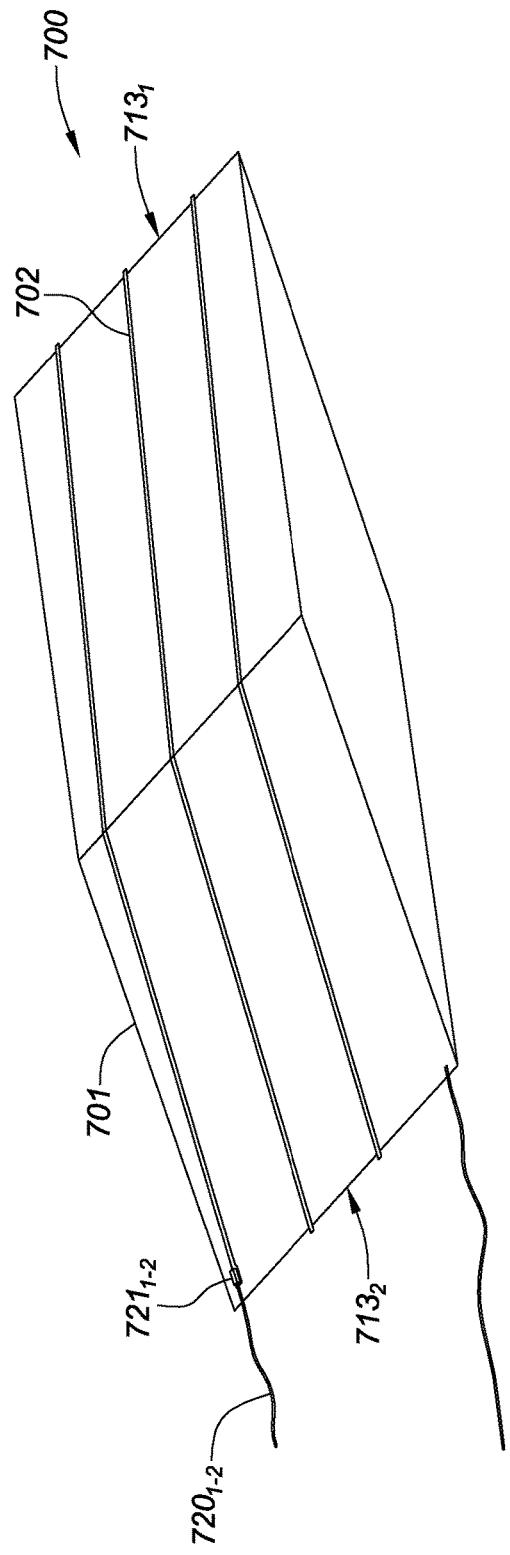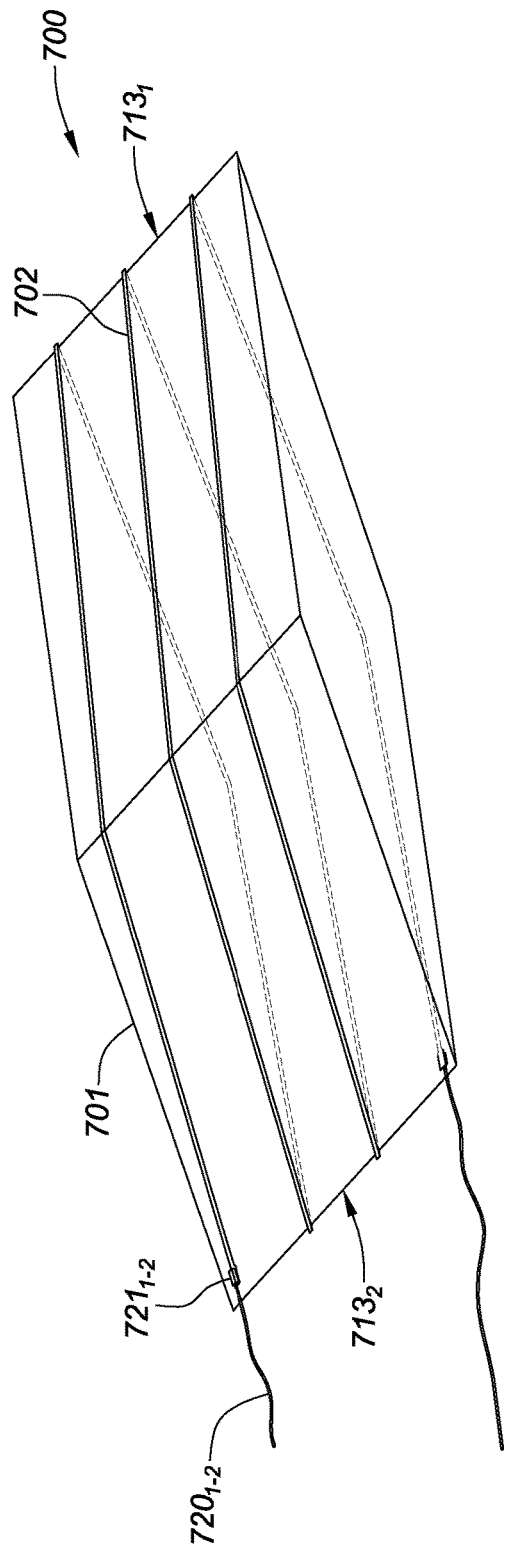

LOCALIZED MAGNETIC FIELD TRANSMITTER

CROSS-REFERENCE TO RELATED APPLICATIONS

This application is a continuation of U.S. application Ser. No. 16/969,551, filed 12 Aug. 2020, which is the National Stage of International Application No. PCT/IB2019/051090, filed 11 Feb. 2019, which claims the benefit of U.S. provisional application No. 62/630,390, filed 14 Feb. 2018, all of which are hereby incorporated by reference as though fully set forth herein.

This application is related to U.S. provisional application No. 62/442,621, filed 5 Jan. 2017, now Patent Cooperation Treaty application no. IB2018/050091, filed 5 Jan. 2018, the entire disclosures of which are hereby incorporated by reference as though fully set forth herein.

This application is related to Patent Cooperation Treaty application no. IB2015/001675, filed 1 Jul. 2015, the entire disclosure of which is hereby incorporated by reference as though fully set forth herein.

This application is related to U.S. provisional application No. 62/098,813, filed 31 Dec. 2014, the entire disclosure of which is hereby incorporated by reference as though fully set forth herein.

This application is related to U.S. provisional application No. 62/020,881, filed 3 Jul. 2014, the entire disclosure of which is hereby incorporated by reference as though fully set forth herein.

This application is related to U.S. provisional application No. 61/900,746, filed 6 Nov. 2013, the entire disclosure of which is hereby incorporated by reference as though fully set forth herein.

BACKGROUND a. Field

The instant disclosure relates to localized magnetic field transmitters, related components, and systems.

b. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart; which can lead to a variety of symptomatic and asymptomatic ailments and even death.

An intravascular catheter may be threaded through a vasculature of a patient to a site where a diagnostic, therapeutic, mapping, and/or ablative procedure to diagnose and/or correct the condition is to be performed. To aid in the delivery of the medical device to the site, and manipulation thereto, sensors (e.g., electrodes) may be placed on the medical device, which can receive magnetic signals that are generated by an electromagnetic field transmitter proximate to the patient. Based on the received signals, an orientation and/or position of the medical device can be computed. However, such magnetic-based localization systems often impede the efficacy of fluoroscopic imaging systems.

The foregoing discussion is intended only to illustrate the present field and should not be taken as a disavowal of claim scope.

BRIEF SUMMARY

Various aspects of the present disclosure are directed to apparatuses for generating a magnetic field for tracking of a target object. Such an apparatus may include a localized magnetic field transmitter that generates a magnetic field and that is substantially X-ray transparent, when used in conjunction with a fluoroscopic imaging system.

One embodiment of the present disclosure is directed to an apparatus for generating a desired magnetic field for tracking of an object within an area of interest. The apparatus includes a low-density magnetic field transmitting element that emits a desired magnetic field in the area of interest and is substantially x-ray translucent. In more specific embodiments, the magnetic field transmitting element includes two or more coils which extend across a common plane, each of the coils are electrically parallel to one another, and extend circumferentially about a common center point.

Various aspects of the present disclosure are directed to a medical positioning system that includes a magnetic field transmitting element, a magnetic field sensing element, and processing circuitry. The magnetic field transmitting element is substantially x-ray translucent, and emits a magnetic field for tracking of an object within an area of interest. The magnetic field sensing element is coupled to a medical catheter, and samples the magnetic field emitted from the magnetic field transmitting element. The processing circuitry is electrically coupled to the magnetic field sensing element and the magnetic field transmitting element. The processing circuitry determines a relative location of the medical catheter based on the magnetic field sampled by the magnetic field sensing element.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which:

FIG. 7A depicts an isometric side-view of a magnetic field transmitter, consistent with various aspects of the present disclosure.

FIG. 7B depicts an isometric side-view of the magnetic field transmitter of FIG. 7A with hidden lines shown, consistent with various aspects of the present disclosure.

Figure 1:
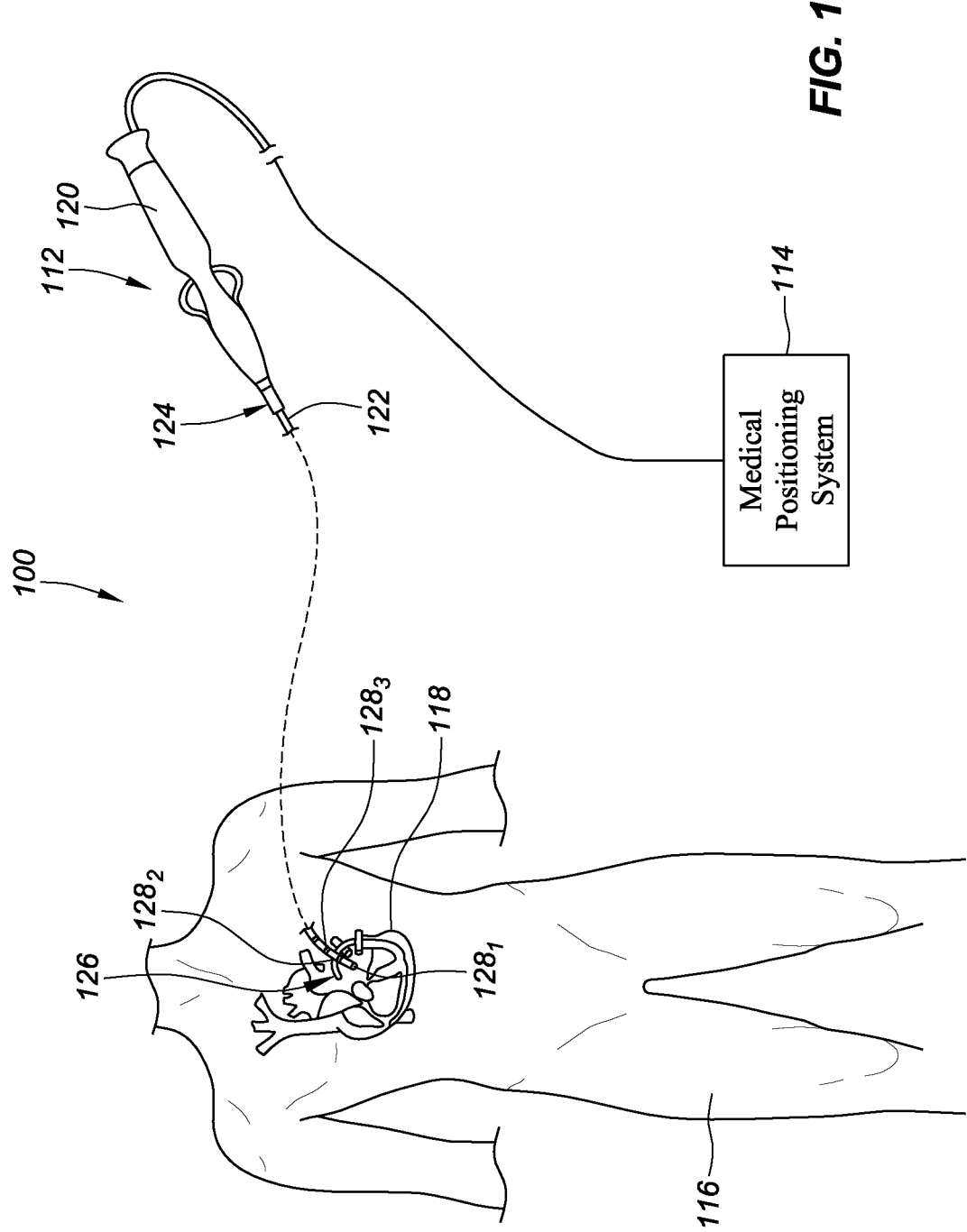
FIG. 1 depicts a diagrammatic view of an exemplary system for performing one or more diagnostic or therapeutic procedures, wherein the system comprises a magnetic field-based medical positioning system, consistent with various aspects of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are applicable to a variety of different types of methods, apparatus, and systems for non-invasive surgical procedure visualization. More specifically, magnetic positioning systems for visualizing an intravascular catheter within a patient's cardiovascular system are disclosed. The magnetic positioning system may include a localized magnetic field transmitter that generates a magnetic field for tracking of an object in an area of interest.

Various aspects of the present disclosure are directed to a magnetic field transmitter which may be used in conjunction with an x-ray imaging system (also referred to as a fluoroscopic imaging system). Specifically, a magnetic field transmitter which may be placed between an x-ray source and an x-ray detector (imager) of an x-ray imaging system and minimally impede a resulting x-ray image. X-ray imaging directs photons at a target tissue region of a patient's body to visualize cellular and histological structures therein. The patient's body absorbs photons from the x-ray source in relation to the electron density of the tissue the photons are passing through (i.e., tissue density). Accordingly, high-density structures (e.g., bones) absorb more photons than low-density structures (e.g., tissue). The change in density is visualized in the resulting x-ray image via contrasting gradients. Aspects of the present disclosure are directed to magnetic field transmitters with low-density designs to mitigate visualization of the transmitters in an x-ray image (also referred to as a fluoroscopic image).

In one embodiment, consistent with the present disclosure, a magnetic positioning system for tracking of an object, via a magnetic field, is disclosed including a localized magnetic field transmitter that generates a magnetic field in an area of interest and that minimally absorbs light in the x-ray spectrum. Such an embodiment facilitates the use of the magnetic field transmitter in applications where the transmitter is used within an image frame of a fluoroscopic imaging system.

In one example embodiment, a surgical suite includes a fluoroscopic imaging system for imaging target regions of a patient's anatomy, and a magnetic positioning system for visualizing an intravascular catheter within the patient's cardiovascular system. The magnetic positioning system includes a localized magnetic field transmitter that generates a magnetic field for tracking a location of an electromagnetic sensor (e.g., within, or on, the catheter). Due to the relatively small magnetic field emitted from the localized magnetic field transmitter, the transmitter must be placed in close proximity to the target region of the patient's anatomy, where catheter tracking is desired. Often times, this places the localized magnetic field transmitter within an image frame of the fluoroscopic imaging system, which may negatively impact the diagnostic benefit of the image. To minimize the impact of the localized magnetic field transmitter on the fluoroscopic imaging systems efficacy, aspects of the present disclosure are directed to transmitters with x-ray opacity (or more desirably x-ray translucency).

Details of the various embodiments of the present disclosure are described below with specific reference to the figures. While the present invention is not necessarily so limited to medical devices, various aspects of the present disclosure may be appreciated through a discussion of examples using these contexts.

FIG. 1 depicts a diagrammatic view of an example surgical system 100 for performing one or more diagnostic or therapeutic procedures, wherein the surgical system comprises a magnetic field-based medical positioning system 114, consistent with various aspects of the present disclosure.

In some embodiments, and with reference to FIG. 1, the surgical system 100 may include a medical device 112 and a medical positioning system 114. The medical device 112 may include an elongated medical device such as, for example, a catheter or a sheath. For purposes of illustration and clarity, the description below will be limited to an embodiment wherein the medical device 112 comprises a catheter (e.g., catheter 112). It will be appreciated, however, that the present disclosure is not meant to be limited to such an embodiment, but rather in other example embodiments, the medical device may comprise other medical devices, such as, for example and without limitation, introducer sheaths, and other non-invasive medical devices. In yet further embodiments, the medical device 112 may be any medical device wherein real-time location-based data may be advantageous to a procedure in which it is used.

With continued reference to FIG. 1, catheter 112 may be inserted into a patient's body 116, such as via the cardiovascular system; and more particularly, into a patient's heart 118. The catheter 112 may include a handle 120, a shaft 122 having a proximal end portion 124 and a distal end portion 126, and one or more sensors 128 mounted in or on the shaft 122 of the catheter 112. As used herein, "sensor 128" or "sensors 128" may refer to one or more sensors 1281, 1282, . . . 128N, as appropriate, and as generally depicted in FIG. 1. In one example embodiment, the sensors 128 are disposed at the distal end portion 126 of the shaft 122. The catheter 112 may further include other conventional components such as, for example and without limitation, a temperature sensor, additional sensors or electrodes, ablation elements (e.g., electrodes for delivering RF ablative energy, high intensity focused ultrasound, etc.), and corresponding conductors or leads.

The shaft 122 can be an elongated, tubular, flexible member for movement within the body 116. The shaft 122 supports, for example and without limitation, sensors and/or electrodes mounted thereon, such as, for example, the sensors 128, associated conductors, and possibly additional electronics used for signal processing and conditioning. The shaft 122 may also permit transport, delivery, and/or removal of fluids (including irrigation fluids, cryogenic ablation fluids, and bodily fluids), medicines, and/or surgical tools or instruments. The shaft 122 may be made from conventional materials such as polyurethane, and define one or more lumens configured to house and/or transport electrical conductors, fluids, or surgical tools. The shaft 122 may be introduced into a blood vessel or other structure within the body 116 through a conventional introducer. The shaft 122 may then be steered or guided through the body 116 to a desired location, such as the heart 118, using means well known in the art.

The sensors 128, mounted in or on the shaft 122 of the catheter 112, may be provided for a variety of diagnostic and therapeutic purposes including, for example and without limitation, electrophysiological studies, pacing, cardiac mapping, and ablation. In an example embodiment, one or more of the sensors 128 are provided to perform a location or position sensing function. More particularly, and as will be described in greater detail below, one or more of the sensors 128 can be a positioning sensor that provides information relating to the location (e.g., position and orientation) of the catheter 112, and the distal end portion 126 of the shaft 122 thereof, in particular. Accordingly, in such an embodiment, as the catheter 112 is moved along a surface of the heart 118 and/or about the interior of the heart, the sensor(s) 128 may be used to collect location data points that correspond to the surface of, and/or other locations within, the heart (or other structure of interest). These location data points can then be used for a number of purposes such as, for example and without limitation, the construction of surface models of the structure of interest or navigation. For purposes of clarity and illustration, the description below will be with respect to an embodiment wherein a single sensor 128 of the catheter 112 comprises a positioning sensor. It will be appreciated, however, that in other example embodiments, which remain within the spirit and scope of the present disclosure, the catheter 112 may comprise more than one positioning sensor as well as other sensors or electrodes configured to perform other diagnostic and/or therapeutic functions. In some embodiments, one or more sensors 128 may determine the six degrees of freedom of the catheter tip. As will be described in greater detail below, the sensor 128 may include a pair of leads extending from a sensing element thereof (e.g., a coil) that electrically couples the sensor 128 to other components of the system 100, such as, for example, medical positioning system 114.

Figure 2:
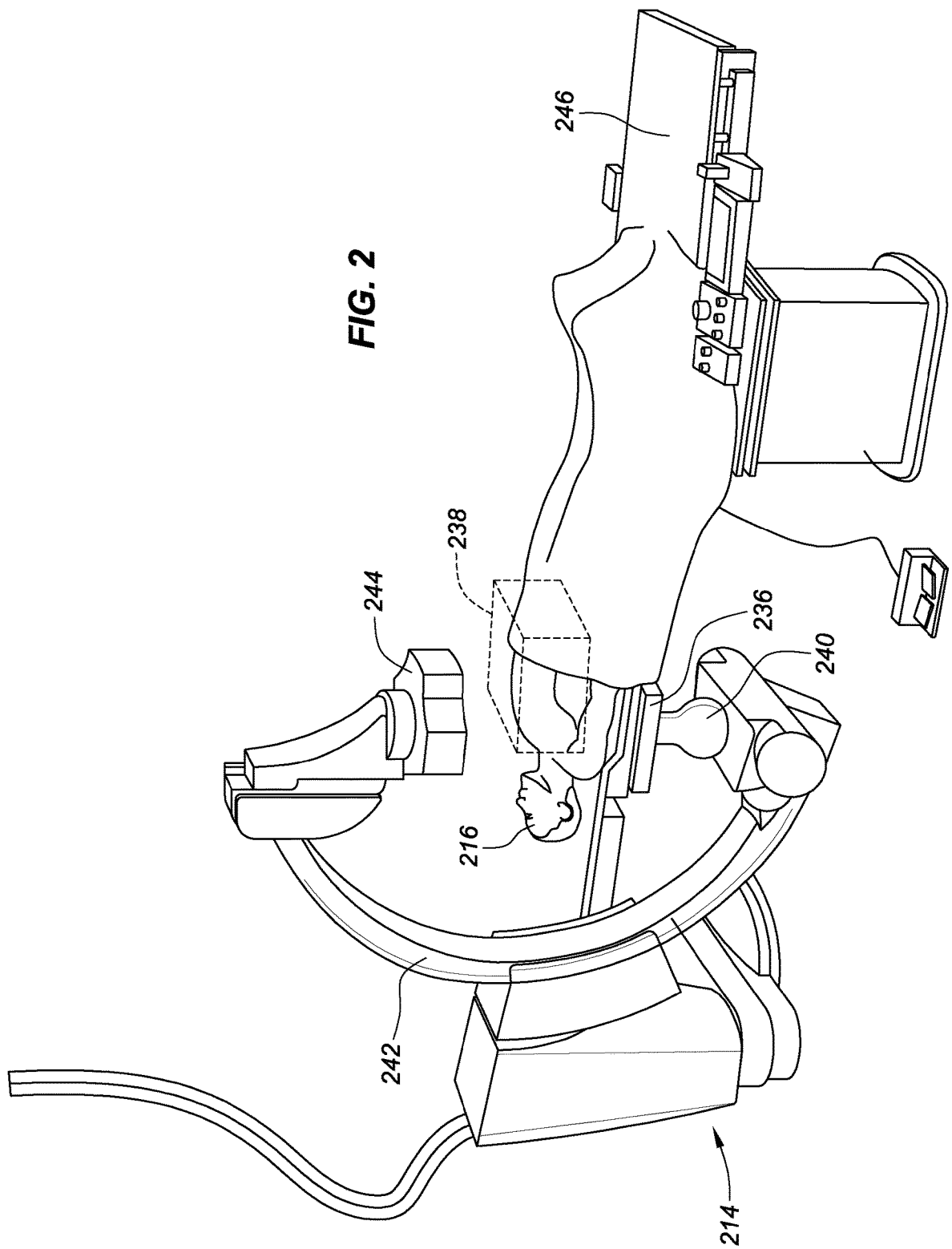
FIG. 2 depicts an isometric side-view of a medical positioning system, consistent with various aspects of the present disclosure.

With reference to FIGS. 1 and 2, medical positioning system 114/214 will now be described. The medical positioning system 114/214 can be provided for determining a position and/or orientation of a sensor 128 at a distal end portion 126 of catheter 112; and thus, the position and/or orientation of the distal end portion of the catheter 112 itself. In some embodiments, the medical positioning system 114/214 may comprise a magnetic-field based system such as, for example, the MEDIGUIDE™ system from MediGuide Ltd. (now owned by Abbott), and as generally shown and described in one or more of U.S. Pat. Nos. 6,233,476; 7,197,354; and 7,386,339, each of which are incorporated herein by reference.

In some embodiments, and in general terms, the medical positioning system 114/214 comprises, at least in part, a magnetic field transmitter 236 for generating a magnetic field for tracking of an object(s) (e.g., a distal portion of catheter 112). The magnetic field transmitter 236 may generate a low-strength magnetic field(s) in and around the patient's chest cavity (e.g., an area of interest 238 during a cardiac surgical procedure), as shown in FIG. 2. In such an embodiment, and as briefly described above, the catheter 112 includes one or more positioning sensors that detect characteristics of the magnetic field(s) emitted by the magnetic field transmitter 236, when the one or more sensors 128 are disposed within the area of interest 238. The sensor(s) 128, which in some example embodiments comprise a magnetic coil, are communicatively coupled with processing circuitry. The sensor generates a signal corresponding to the sensed characteristics of the magnetic field(s) to which the magnetic coil is exposed, which is further transmitted to the processing circuitry. The processing circuitry, responsive to the detected signal, calculates a three-dimensional position and orientation for the sensor 128 based on the detected characteristics of the magnetic field and an input to the magnetic field transmitter 236. Thus, the medical positioning system 114/214 enables real-time tracking of each magnetic sensor 128 of the catheter 112 in space; and thereby, real-time tracking of the catheter 112.

As shown in FIG. 2, magnetic field transmitter 236 may be located underneath or above an operating table 246, between an x-ray source 240 and the operating table 246. For example, the magnetic field transmitter 236 can be coupled to the operating table 246. In some embodiments, as discussed herein, the magnetic field transmitter 236 can be a mobile device, which can be placed on a chest of the patient and used to generate the magnetic field for tracking of the object. In yet other embodiments, aspects of the present disclosure can be directed to a magnetic field transmitter 236 which includes one or more transmitters on various sides of an area of interest 238.

Aspects of the present disclosure address challenges associated with a medical positioning system 214 generating a magnetic field for tracking an object in a target area, while also maintaining fluoroscopic image visibility within the target area for a fluoroscopic imaging system. This may be particularly difficult where a magnetic field transmitter 236 generates a low-strength magnetic field(s) necessitating proximal placement of the transmitter to an area of interest 238. The fluoroscopic imaging system includes an x-ray source 240 and an x-ray detector 244 located on opposite sides of c-arm 242. The fluoroscopic imaging system is often used in conjunction with a magnetic-based or impedance-based medical positioning system 214. The x-ray source 240 of the fluoroscopic imaging system directs photons through an area of interest 238 to an x-ray detector (imager) 244 opposite the x-ray source. Where high-density objects are located between the x-ray source and x-ray detector, photons are absorbed by the high-density object and the object is visible in the resulting x-ray image. This object may then obscure details of a target tissue region of a patient's body, such as cellular and histological structures. Accordingly, various aspects of the present disclosure are directed to reducing the density of the magnetic field transmitters 236 to minimize x-ray absorption.

In various embodiments of the present disclosure, a catheter may include one or more magnetic sensors. The catheter may also include electrode sensors which function in conjunction with an impedance-based tracking system. Accordingly, such an embodiment relies upon a hybrid localization system (i.e., a combination of impedance-based and magnetic-based tracking).

While in some applications, a magnetic field transmitter 236 of a medical positioning system 214 may be positioned outside of an image field for a fluoroscopic imaging system, a clinician during a non-invasive, intravascular surgical procedure often re-orients the fluoroscopic imaging system during the procedure to achieve a desired image field. For example, x-ray source 240, the c-arm 242, the x-ray detector 244, as well as the operating table 246 may all be re-oriented with respect to the magnetic field transmitter 236. Accordingly, the necessity of placing the magnetic field transmitter in close proximity to a target area 238 creates a high likelihood that the transmitter will, in at least some orientations of the fluoroscopic imaging system, be within the image frame. By reducing the density of the transmitter, the transmitter may be rendered substantially transparent in images taken by the fluoroscopic imaging system.

In some example embodiments, a magnetic field transmitter 236 may be coupled to c-arm 242, allowing for the movement of the magnetic field relative to the patient examination table 246 and the patient 216. Such aspects may still require the transmitter to utilize low-density materials.

In one example embodiment, medical positioning system 214 may further include an impedance-based system for determination of a position and/or orientation of a catheter. However, in some previous approaches, the impedance-based system can suffer from a shift and/or drift of the coordinates determined through the impedance-based system. In addition, a distorted representation of a geometry of the heart can be generated when using an impedance based system. For instance, electrical currents used in an impedance-based system can travel three-dimensionally along a path of least resistance. As such, part of the electrical currents can leave a transverse plane with blood flow, for example, through an impedance transfer—which can result in a distorted representation of the geometry of the heart. When the impedance-based system is used in conjunction with a magnetic tracking system, as disclosed herein, the above problems may be corrected for. Due to the accuracy of the magnetic tracking system, the magnetic tracking system may be used to correct for the shift and/or drift associated with coordinates determined through the impedance-based system.

In one example embodiment, consistent with various aspects of the present disclosure, a magnetic field transmitter 236 produces a decaying magnetic field and is positioned proximate to an area of interest 238. In such an embodiment, the size of a magnetic field produced outside an area of interest 238, by the magnetic field transmitter 236, is reduced. The reduced magnetic field outside the area of interest minimizes the likelihood of magnetic field disturbances by ferrous/conductive objects, located outside the area of interest 238, may disturb the magnetic field within the area of interest.

In some approaches, an eddy current caused by a conductive object (e.g., a c-arm 242), in proximity to an area of interest 238, can be factored out when determining a location of the catheter 212. Specifically, the medical positioning system 214 may be calibrated in order to account for the effect on the magnetic field within an area of interest 238 due to a conductive object(s) in proximity to the area of interest. For example, the disturbance caused to the magnetic field via the eddy currents can be factored out when determining a position of an object located in an area of interest; however, such calibration techniques are only effective for static conductive objects (e.g., large capital equipment within the operating suite). Alternatively, or combined with such calibration techniques, embodiments of the present disclosure can avoid creation of eddy currents due to conductive objects altogether, thereby avoiding the need for calibrating a medical positioning system to compensate for such magnetic distortions. Such embodiments may reduce installation time and decrease installation complexity.

In one embodiment, where a localized magnetic field transmitter 236 is assembled onto an aperture on or over an operating table (a non-mobile configuration), the various magnetic coils that comprise the localized magnetic field transmitter 236 may be significantly more spaced apart than in the mobile configuration. In such embodiments, an area of interest 238 can be a square, cylinder, pyramidal shape, etc. (based on the positioning of the magnetic coils), and the size of the area of interest may vary depending on the application. For example, where it is desirable to track a catheter from insertion within a femoral vein within a leg to a location within the patient's heart, the area of interest 238 may be a meter wide, a meter long, and at least one third a meter deep.

In further more specific embodiments, an area of interest 238 for localization and visualization of a medical device within a patient may include multiple segments that may be activated and deactivated based on the relative location of the medical device within the patient. In one example embodiment, it may be desirable to track a catheter from insertion within a femoral vein within the leg to a location within the patient's heart. To mitigate the need to adjust both a fluoroscopic imaging system, and the localized magnetic field transmitter 236, a number of transmitters may be positioned along a predicted path of the catheter. As such, a clinician and/or magnetic field controller may deactivate segments of the magnetic field transmitter where localization of a catheter is taking place in another segment. As one specific example, where a catheter includes one or more magnetic sensors being localized in proximity to lower extremities of patient 216, other segments of the magnetic field may be deactivated (e.g., de-powering magnetic coils in segments associated with the patient's upper extremities and chest). As the catheter moves toward another segment of the magnetic-field based mapping system, multiple segments may operate simultaneously (at least temporarily until the magnetic sensors in the catheter may be accurately located with only the magnetic coils associated with a chest cavity segment).

Figure 3:
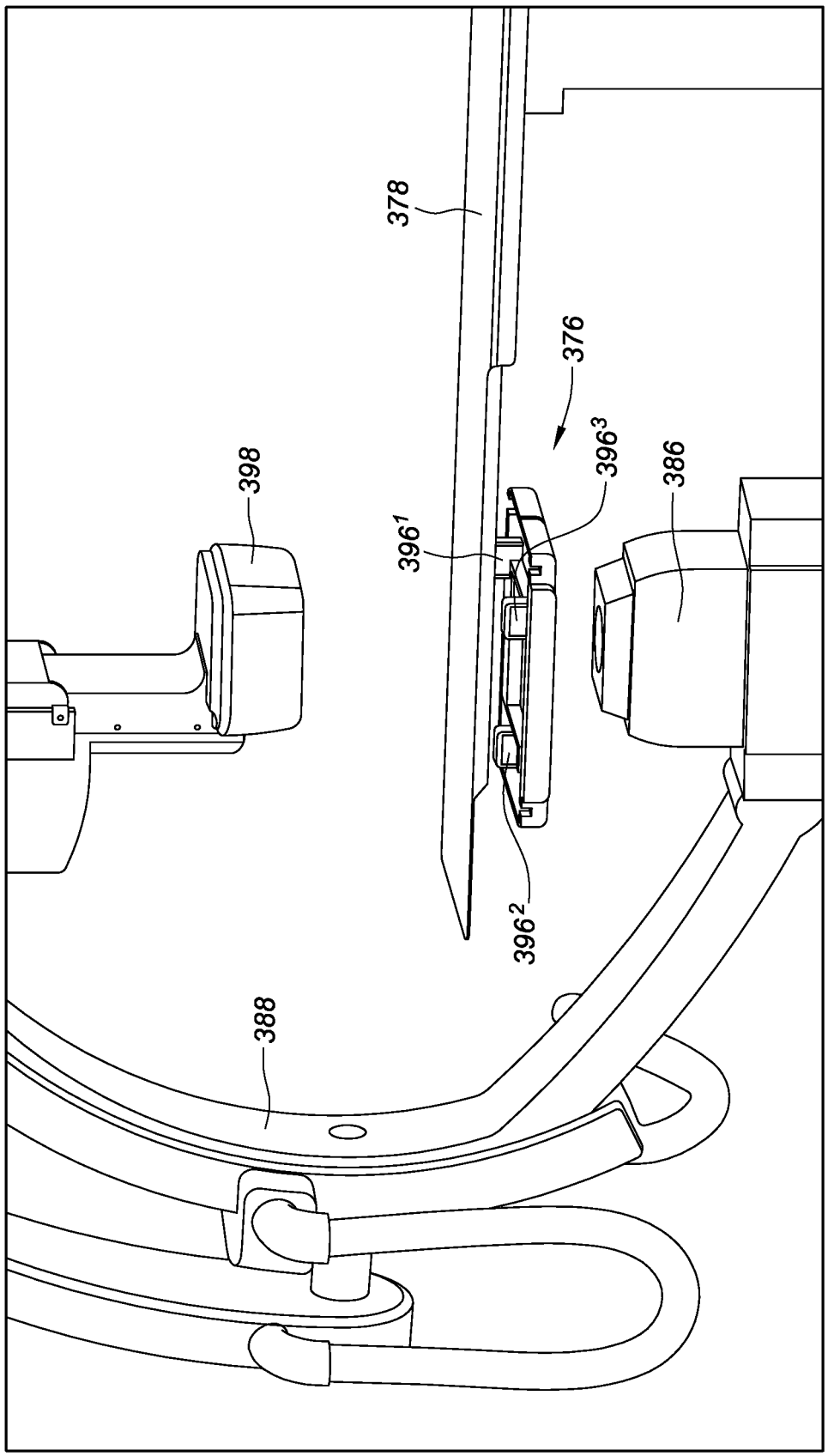
FIG. 3 depicts a partial, more detailed, isometric side-view of the medical positioning system in FIG. 2, consistent with various aspects of the present disclosure.

FIG. 3 depicts a partial, detailed, isometric view of the medical positioning system in FIG. 2, consistent with various aspects of the present disclosure. As discussed herein, the medical positioning system may include a localized magnetic field transmitter 376. The localized magnetic field transmitter 376 can be located between a patient examination table 378 and a magnetic field-disrupting component (e.g., x-ray source 386, c-arm 388). The localized magnetic field transmitter 376 can include a plurality of magnetic transmitting elements $396^{1-3}$. In some embodiments, the plurality of magnetic transmitting elements $396^{1-3}$ can be located beneath patient examination table 378. In yet other embodiments, the plurality of magnetic transmitting elements $396^{1-3}$ can be located anywhere within the operating suite, so long as the plurality of magnetic transmitting elements $396^{1-3}$ are in close proximity to an area of interest 238 (as shown in FIG. 2).

In various embodiments of the present disclosure, magnetic transmitting elements $396^{1-3}$ of localized magnetic field transmitter 376 may be positioned in such a way as to create a clear path along a vertical axis, for example, through an area of interest. In such an embodiment, the x-rays from x-ray source 386 can pass between the magnetic transmitting elements, through the patient examination table 378, to the X-ray detector 398 without being (substantially) absorbed by high-density components of the magnetic transmitting elements. As discussed above, high-density components within the path of the x-ray light absorb photons and may obscure the areas of interest in the resulting x-ray image.

In some embodiments, as discussed herein, magnetic transmitting elements $396^{1-3}$ may be mounted in different locations relative to a path of x-rays from the x-ray source 386 to the X-ray detector 398. For example, the magnetic transmitting elements $396^{1-3}$ can be mounted around the path. In some embodiments, the magnetic transmitting elements $396^{1-3}$ can be mounted with different orientations with respect to the x-ray path. For example, the magnetic transmitting elements $396^{1-3}$ can be mounted at an angle with respect to the x-ray path. In some embodiments, the magnetic transmitting elements $396^{1-3}$ can direct a magnetic field towards a particular point. In one example, the particular point can be inside the area of interest 238 (as shown in FIG. 2). In addition, the magnetic transmitting elements $396^{1'}$ can be rotated with respect to one another. For instance, the magnetic transmitting elements $396^{1'}$ can be mounted at a same angle and can be rotated with respect to one another, such that they are directed toward a central axis of the x-ray path.

In various embodiments consistent with the present disclosure, magnetic transmitting elements $396^{1-3}$ can be split center transmitters and may create an array of magnetic transmitting elements with magnetic field outputs that are synchronized. In further embodiments, the magnetic transmitting elements $396^{1-3}$ can operate independently, and in parallel to one another. In applications where precise control of an area of interest is desirable, aspects of the present disclosure are directed to positioning all of the magnetic transmitting elements to a single focal point in space. Yet further embodiments of the present disclosure are directed to magnetic transmitting elements $396^{1-3}$ that are flat coils. Moreover, in some embodiments these flat coils may also integrate parallel windings to reduce resistance and to further minimize a z-height of the magnetic transmitting elements. The parallel windings reduce the density of the magnetic transmitting elements in a z-direction. A number of these substantially flat coil magnetic transmitting element designs, as disclosed herein, may be "side-firing" magnetic coils (i.e., producing a magnetic field that propagates a magnetic field in a direction that is perpendicular to a top surface of the magnetic transmitting elements). These side-firing magnetic transmitting elements may include vias of 1 centimeter in length or longer. Alternatively, the coils may be wrapped coil segments to facilitate x-ray translucency. To further improve x-ray attenuation, the magnetic transmitting elements may have coils with limited linear ascent/descent angles, relative to an x-ray image plane. Further, the coils of the magnetic transmitting elements may have a width up to 30 centimeters to further improve the density of the coils, relative to an x-ray image plane. In yet further more specific embodiments, the plurality of windings may be configured across various axes to facilitate x-ray imaging across various planes.

In some embodiments, a side-firing magnetic transmitting element may be integrated with a flat coil magnetic transmitting element.

In various embodiments of the present disclosure, magnetic transmitting element 396 includes one or more coils that create magnetic fields in response to a flow of electrical current therethrough. A change to the current driving the coil can control the produced magnetic field. For example, a reduced current through the coil results in a reduced magnetic field strength. Similarly, an increased current through the coil results in an increased magnetic field strength. When placed in close proximity to one another, magnetic transmitting elements $396^{1-3}$ produce an amplified magnetic field, or a rapidly decaying magnetic field (depending on the relative polarities of the fields produced by each magnetic transmitting element).

In some embodiments, a coil of the magnetic transmitting elements $396^{1-3}$ may be formed of various thicknesses of wire (or traces) and various numbers of windings. In some examples, as a wire thickness and various numbers of windings of the magnetic transmitting element's coil changes, a range and/or strength of the magnetic field may vary. As such, the numbers of windings of the coil may be chosen to create a magnetic field that is sized for a desired application. Importantly, it is desirable to limit the size of the magnetic field so that ferrous objects within the operating suite do not enter the magnetic field, and cause magnetic field distortions (e.g., eddy currents) therein.

A magnetic-based localization system may include a magnetic-field sensor coupled to a distal tip of a catheter and one or more magnetic transmitting elements, both of which are communicatively coupled to medical positioning controller circuitry, via one or more cables, or wireless communication means. The sensor provides electrical signals to the controller for determination of the three-dimensional position and/or orientation of the sensor (and the distal tip of the catheter). In more specific embodiments, the medical positioning controller circuitry may produce an image, and transmit it to a display, that overlays the catheter position and orientation over a Magnetic Resonance Image, an x-ray image, or other image-type data (such as ultrasound) to facilitate the clinician's understanding of the location of the catheter within the patient's body.

To prevent magnetic interference of the signals transmitted through a catheter shaft of the medical device, the cables may be magnetically shielded, and/or may utilize a twisted-pair configuration, to prevent interference from magnetic field-disrupting components or the emitted magnetic field itself. In yet other embodiments, the sensor may include wireless transceiver circuitry to facilitate wireless communication of position and orientation data of the catheter to medical positioning controller circuitry.

Some embodiments of the present disclosure may be compatible with cardiac mapping systems such as, for example, the ENSITE VELOCITY™ cardiac mapping system.

Figure 4:
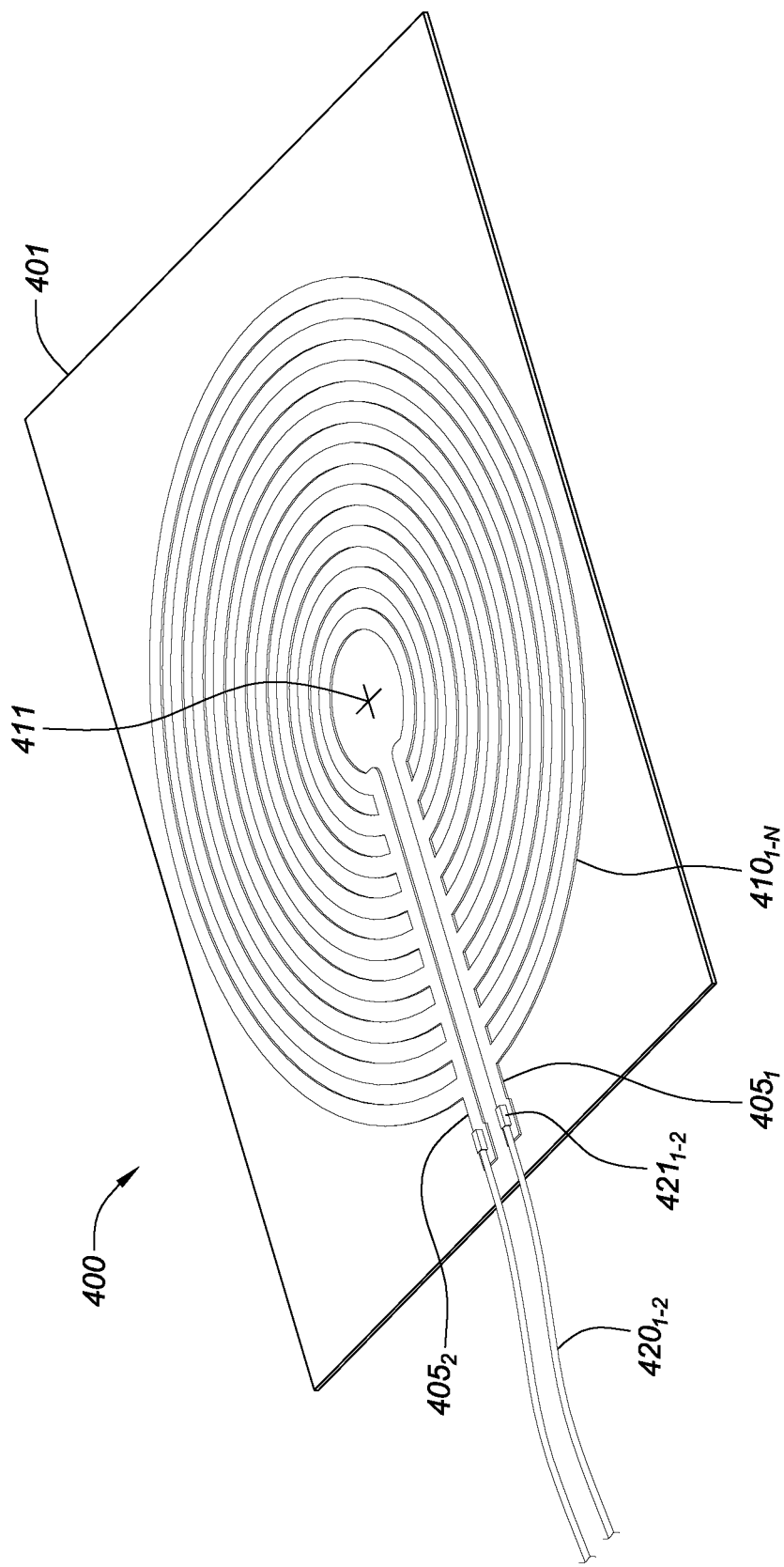
FIG. 4 depicts an isometric side-view of a magnetic field transmitter for a medical positioning system, consistent with various aspects of the present disclosure.

FIG. 4 depicts an isometric side-view of a magnetic field transmitting element 400, consistent with various aspects of the present disclosure.

The magnetic field transmitting element generates a magnetic field for tracking of an object, consistent with various aspects of the present disclosure. The magnetic field transmitting element 400 may include one or more coils $410_{1-N}$ which may be driven by a current to produce a magnetic field that extends through a center point 411 of the transmitting element 400. Depending on the polarity of the current, the magnetic field lines extend up through the center point 411 or down through the center point. The strength of the magnetic field, for a given current, is dependent upon the number of windings. The magnetic field transmitter may be coupled to a power source via one or more lead wires $420_{1-2}$. The lead wires are coupled to the transmitting element at solder pads via solder $421_{1-2}$, or other equivalent electrical coupling techniques. Input/output traces $405_{1-2}$ of the transmitting element are coupled to the plurality of coils $410_{1-N}$ which circumferentially extend approximately one rotation around center point 411. Each of the individual coils amplify the resulting magnetic field that extends perpendicular to a top surface of substrate 401. By utilizing concentric coils in a single plane (i.e., no coils being wound longitudinally along a central axis of the magnetic field transmitter), a z-depth of the transmitter may be minimized. Moreover, as the plurality of coils $410_{1-N}$ of the present embodiment are placed in parallel to one another, as opposed to in series, damage to one or more of the coils within the transmitter will not result in the complete failure of the transmitter. Instead, damage to the coils will merely reduce the produced magnetic field for a given drive current. Using this method may also allow for the use of low-impedance coils, achieving the same magnetic field strength as a series winding coil.

Where the transmitting element is coupled to substrate 401, and a power source is also coupled to the same substrate, printed electrical traces may be used to electrically couple the power source to the transmitting element.

Figure 5A:
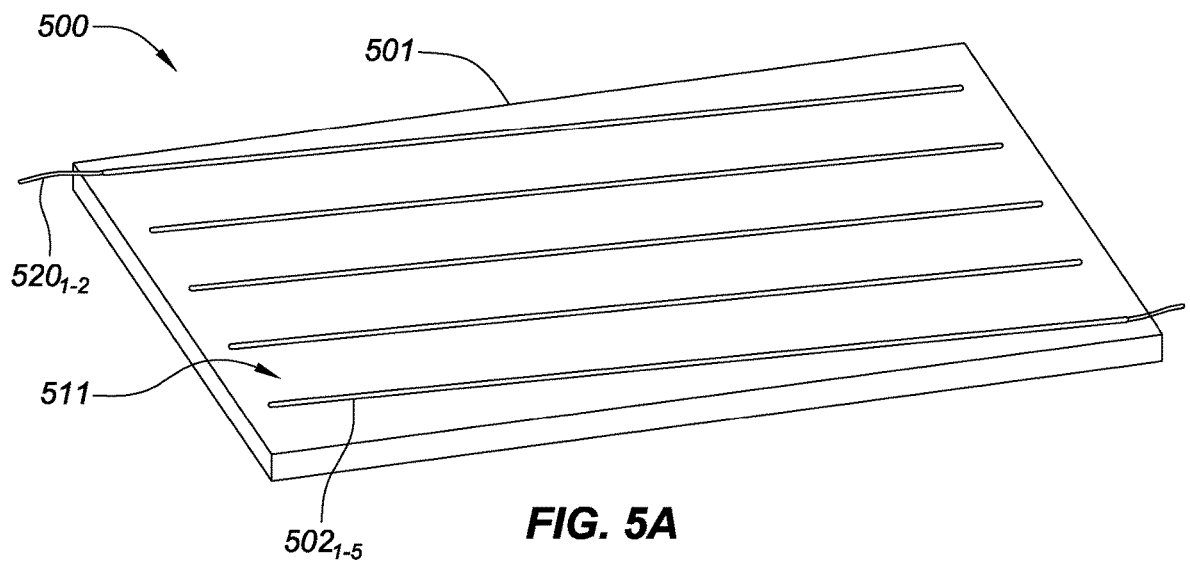
FIG. 5A depicts an isometric side-view of a magnetic field transmitter, consistent with various aspects of the present disclosure.
Figure 5B:
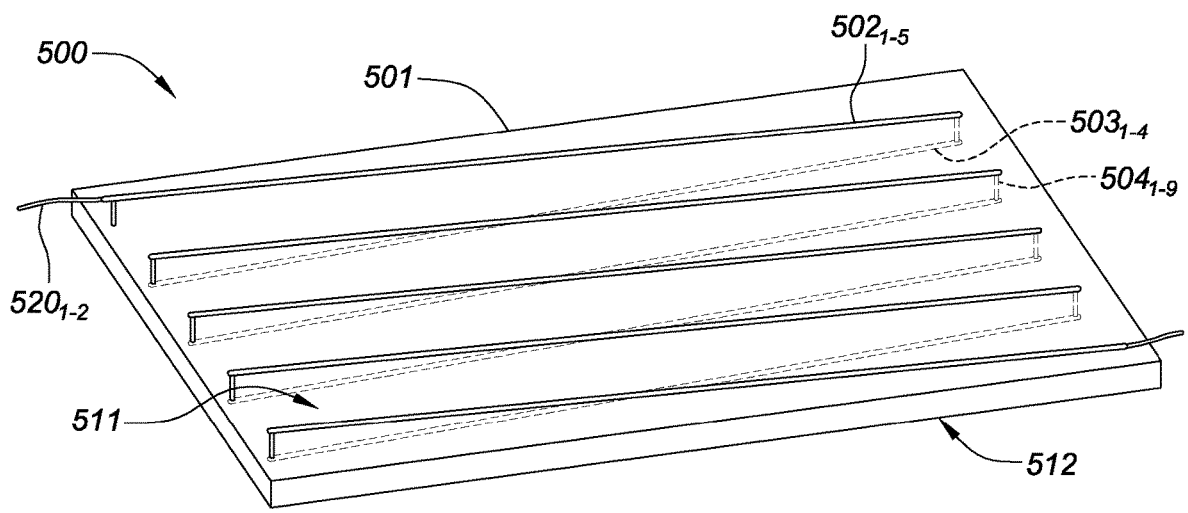
FIG. 5B depicts an isometric side-view of the magnetic field transmitter of FIG. 5A with hidden lines shown, consistent with various aspects of the present disclosure.
Figure 5C:
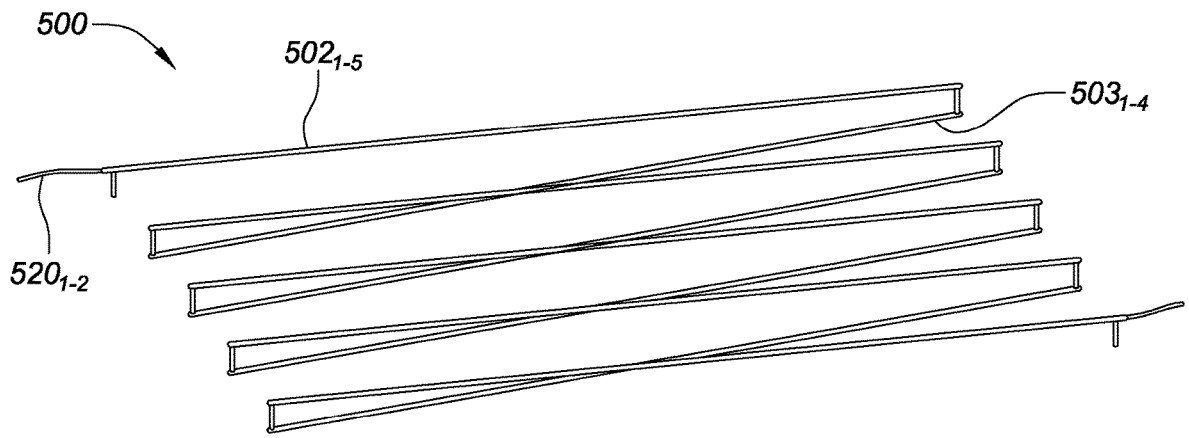
FIG. 5C depicts an isometric side-view of the magnetic field transmitter of FIG. 5A with a substrate hidden, consistent with various aspects of the present disclosure.
Figure 5D:
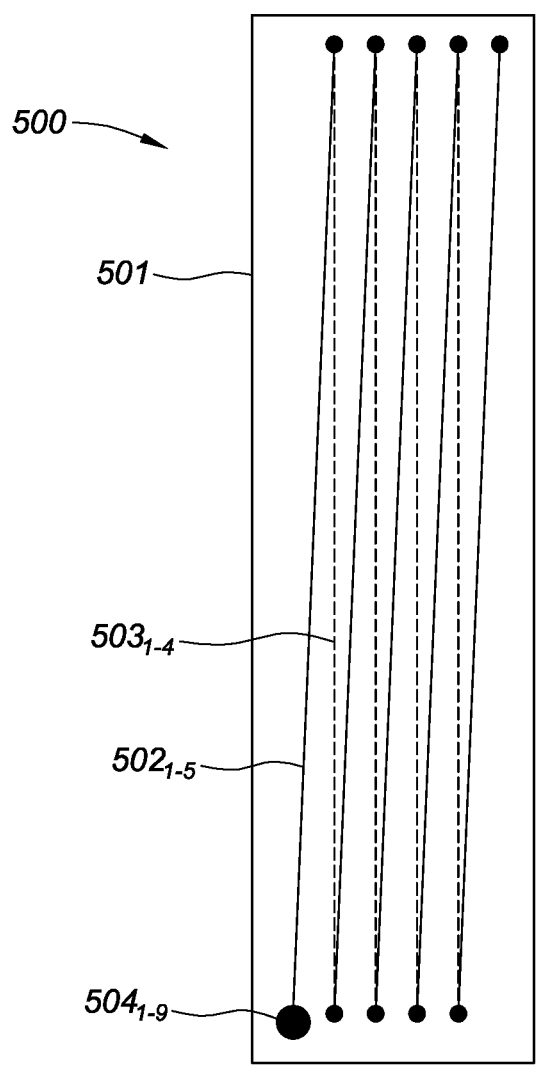
FIG. 5D depicts a top-view of the magnetic field transmitter of FIG. 5A with hidden lines shown, consistent with various aspects of the present disclosure.

FIG. 5A depicts an isometric side-view of a magnetic field transmitter 500, FIG. 5B is an isometric side-view of the magnetic field transmitter with hidden lines shown, FIG. 5C shows the magnetic field transmitter with a substrate 501 hidden, and FIG. 5D is a top-view of the magnetic field transmitter of FIG. 5A with hidden lines shown, consistent with various aspects of the present disclosure. The magnetic field transmitter 500 includes a multi-layer substrate 501. The multi-layer substrate is compatible with known printed circuit board manufacturing techniques. First electrical traces $502_{1-5}$ may be printed to a first layer 511 of the substrate. Second electrical traces $503_{1-4}$ may be printed to a second layer 512 of the substrate. The first and second electrical traces are electrically coupled to one another with vias $504_{1-9}$, which extend through the substrate 501 between the first and second layers. The electrical traces and vias form a coil which extends parallel relative to a top surface of the substrate, while minimizing a z-height of the magnetic field transmitter 500. Both sides of the resulting coil may be electrically coupled to a power source via lead wires $520_{1-2}$.

When exposed in an x-ray image frame, where the x-ray source and x-ray detector are aligned with a top and bottom surface of magnetic field transmitter 500, vias $504_{1-9}$ are the most x-ray visible aspect of the transmitter (see, e.g., FIG. 5D). However, the offset traces on the first and second layers of the substrate mitigates x-ray visibility of the traces. The embodiments disclosed in FIGS. 6A-7B are directed to further reducing the x-ray visibility of such a side-firing, magnetic field transmitter.

Figure 6A:
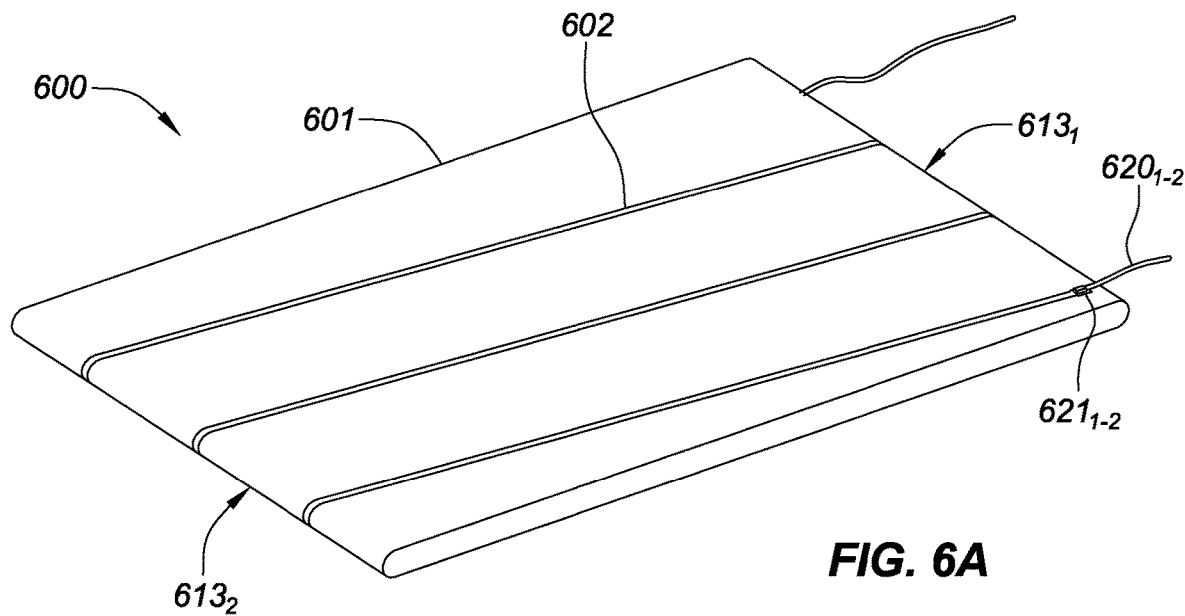
FIG. 6A depicts an isometric side-view of a magnetic field transmitter, consistent with various aspects of the present disclosure.
Figure 6B:
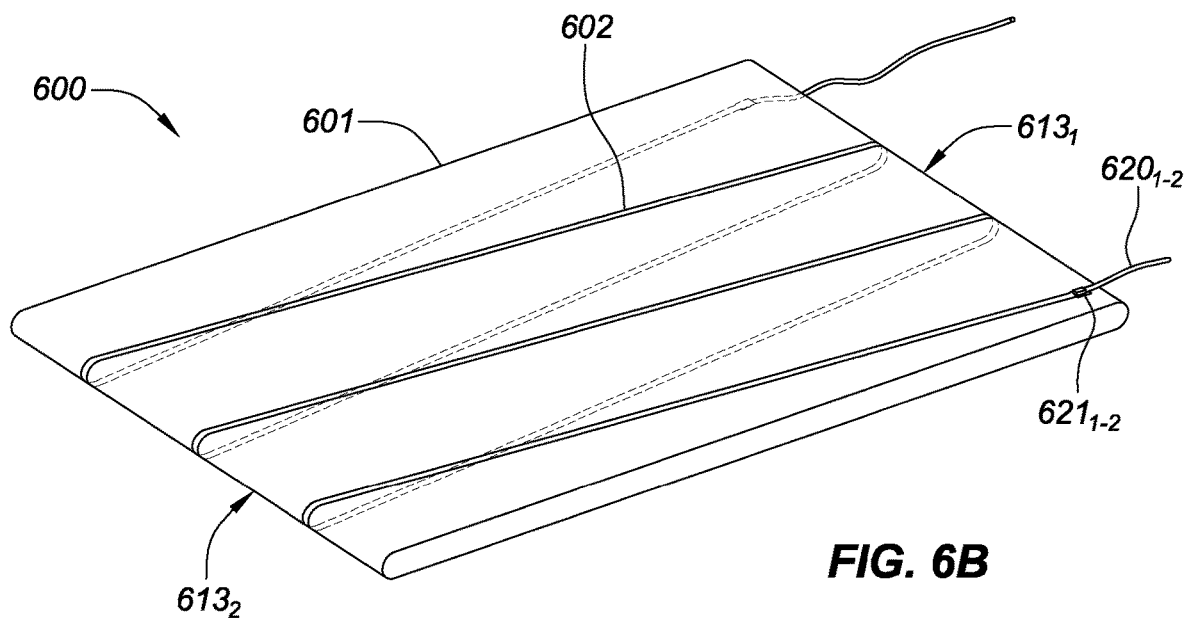
FIG. 6B depicts an isometric side-view of the magnetic field transmitter of FIG. 6A with hidden lines shown, consistent with various aspects of the present disclosure.

FIG. 6A depicts an isometric side-view of a magnetic field transmitter 600, and FIG. 6B depicts an isometric side-view of the magnetic field transmitter of FIG. 6A with hidden lines shown, consistent with various aspects of the present disclosure. The magnetic field transmitter includes a substrate 601 to which a wire 602 is wrapped around to form the transmitter. Both sides of the resulting coil may be electrically coupled to a power source via lead wires $620_{1-2}$ (which are soldered $621_{1-2}$, or otherwise coupled to either end of the coil).

Similar to FIGS. 5A-D, the substrate 601 of FIGS. 6A-B is thin to minimize a z-height of the magnetic field transmitter; allowing for placement of the transmitter between a patient and operating table, for example. Reduced z-height is desirable as the transmitter may produce a magnetic field with limited range, requiring placement within a certain distance from a magnetic sensor on a catheter distal tip to properly monitor a location of the catheter within a patient's body.

In the transmitter embodiment disclosed in FIGS. 6A-B, substrate 601 includes rounded edges $613_{1-2}$ which facilitate winding of the wire 602 about the substrate. Moreover, the radius of the wire around the rounded edges reduces the vertical density of wire exposed to an x-ray image frame from above and below. Accordingly, as compared with the magnetic field transmitter 500 of FIG. 5, the transmitter 600 exhibits improved x-ray transparency.

FIG. 7A depicts an isometric side-view of a magnetic field transmitter 700, and FIG. 7B depicts an isometric side-view of the magnetic field transmitter of FIG. 7A with hidden lines shown, consistent with various aspects of the present disclosure. The magnetic field transmitter includes a substrate 701 to which a wire 702 is wrapped around to form the transmitter. Both sides of the resulting coil may be electrically coupled to a power source via lead wires $720_{1-2}$ (which are soldered $721_{1-2}$, or otherwise coupled to either end of the coil).

The thin, diamond-shaped substrate 701 minimizes an overall z-height of the magnetic field transmitter 700, while also optimizing various sides of the substrate for x-ray imaging.

In the transmitter embodiment disclosed in FIGS. 7A-B, wire 702 is wound about substrate 701 at edges $713_{1-2}$. The edges reduce the density of wire aligned vertically with, and exposed, to an x-ray image frame perpendicular to a top of the transmitter. The magnetic field transmitter 700 exhibits improved x-ray transparency to a number of facets.

In some embodiments of the present disclosure, a substrate of the magnetic field transmitter may be comprised of a rigid foam, or other low-density material (e.g., polyamide (nylon), polycarbonate, and low-density polyethylene).

Consistent with various embodiments of the present disclosure, the magnetic field transmitter 700 of FIG. 7A-B may also be manufactured using a multi-layer printed circuit board design.

Figure 8:
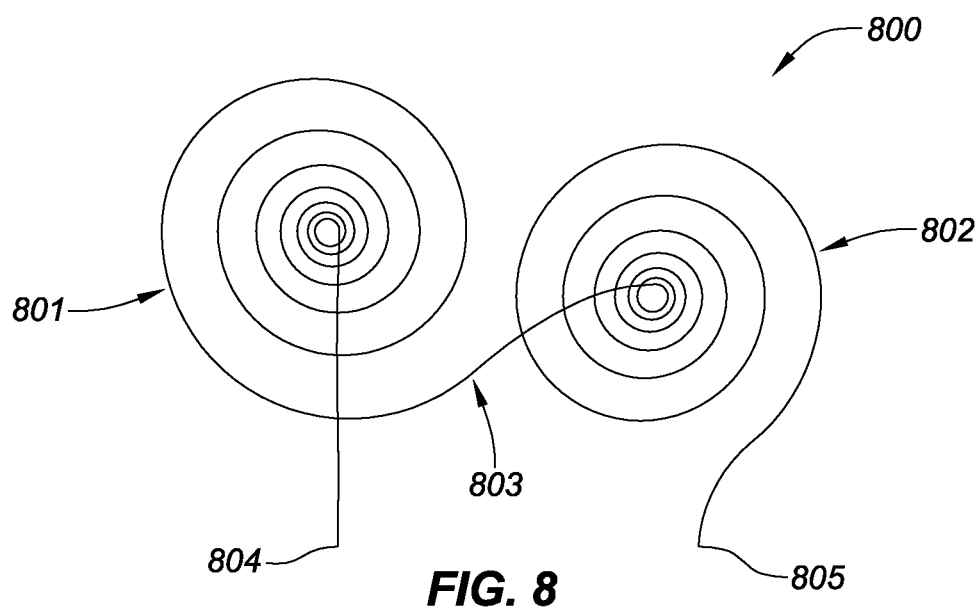
FIG. 8 is a diagrammatic view of a magnetic field transmitter, consistent with various aspects of the present disclosure.

FIG. 8 is a diagrammatic view of a magnetic field transmitter 800, consistent with various aspects of the present disclosure. The magnetic field transmitter includes two coils 801 and 802, which are wound in opposite directions and coupled to one another via a bridge 803. When a power source is coupled to input/outputs 804 and 805, the two coils produce magnetic fields of opposite polarities which create a fast decaying magnetic field. In one embodiment, the transmitter 800 is coiled in a planar manner. That is, the transmitter may be printed on to a circuit board, or otherwise coupled to a surface of a substrate, facilitating a relatively small z-dimension. In other embodiments, the two coils 801 and 802 are wound in the same direction and coupled to one another via a bridge 803. Accordingly, when a power source is coupled to input/outputs 804 and 805, the two coils produce an amplified magnetic field of a single polarity.

By using such a dual coil array configuration with opposing polarities, as shown in FIG. 8, to produce a magnetic field, the field produced quickly diminishes in strength. This type of magnetic field may be referred to as a rapid-decay magnetic field.

In another implementation of a dual coil array, varying current and polarity through each of the coils can shape the magnetic field orientation. As a result, the dual coil array configuration may not only form a magnetic field with varying decay rates, but also form varying field line orientations in space.

Applicant notes that FIGS. 8-11 depict representations of magnetic field transmitters for generating a magnetic field for tracking of a target object, consistent with various aspects of the present disclosure. It is to be understood that the representations of the magnetic field transmitters presented in FIGS. 8-11 would not necessarily reflect the actual shape of the magnetic field transmitters. That is, the magnetic field transmitters would not necessarily be planar. Instead, the magnetic field transmitters may include coils wound longitudinally along an air core. Further examples of magnetic field transmitters are disclosed in U.S. Patent Publication 2016/0287133, the entirety of which is hereby incorporated by reference as though fully set forth herein.

Figure 9:
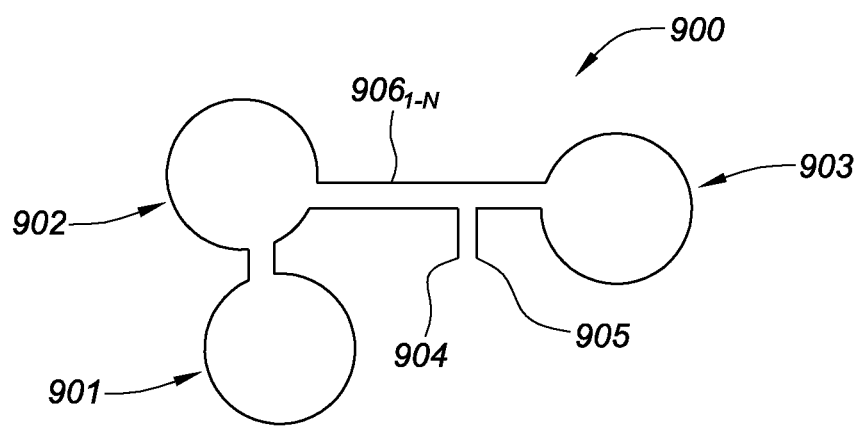
FIG. 9 is a diagrammatic view of a magnetic field transmitter, consistent with various aspects of the present disclosure.

FIG. 9 is a diagrammatic view of a magnetic field transmitter 900, consistent with various aspects of the present disclosure. The magnetic field transmitter includes three coils 901, 902, 903 which are coupled to one another via intermediate traces/wires $906_{1-N}$, and are co-planar relative to one another. In the present embodiment, each of the coils are arranged in series and have the same winding direction. When a voltage is applied across input/outputs 904 and 905, the three coils produce an amplified magnetic field of a single polarity.

Figure 10:
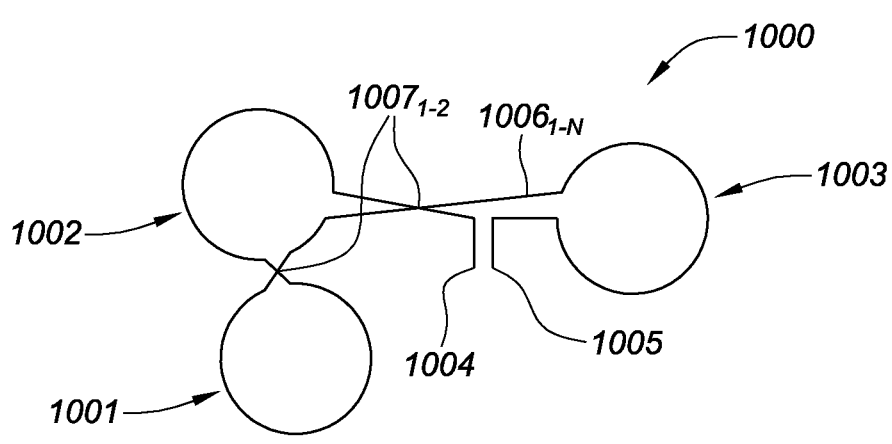
FIG. 10 is a diagrammatic view of a magnetic field transmitter, consistent with various aspects of the present disclosure.

FIG. 10 is a diagrammatic view of a magnetic field transmitter 1000, consistent with various aspects of the present disclosure. The magnetic field transmitter includes three coils 1001, 1002, and 1003 which are coupled to one another via intermediate traces/wires $1006_{1-N}$, and are co-planar relative to one another. In the present embodiment, each of the coils are arranged in series; however, coils 1001 and 1003 have the opposite winding direction of coil 1002. To achieve opposite winding directions between the coils, which are placed in series along a single continuous trace/wire, two or more of the intermediate traces/wires $1006_{1-N}$ have twists $1007_{1-2}$. The twists may be accomplished using a multi-layer printed circuit board, where two intermediate traces $1006_{1-N}$ intersect one another and one of the traces is extended temporarily to another layer via a pair of vias. When a voltage is applied across input/outputs 1004 and 1005, the coils 1001 and 1003 produce an amplified magnetic field of a first polarity, and coil 1002 produces another magnetic field of a second polarity. The first and second magnetic field polarities cause a resulting magnetic field with rapidly-decaying characteristics.

Figure 11:
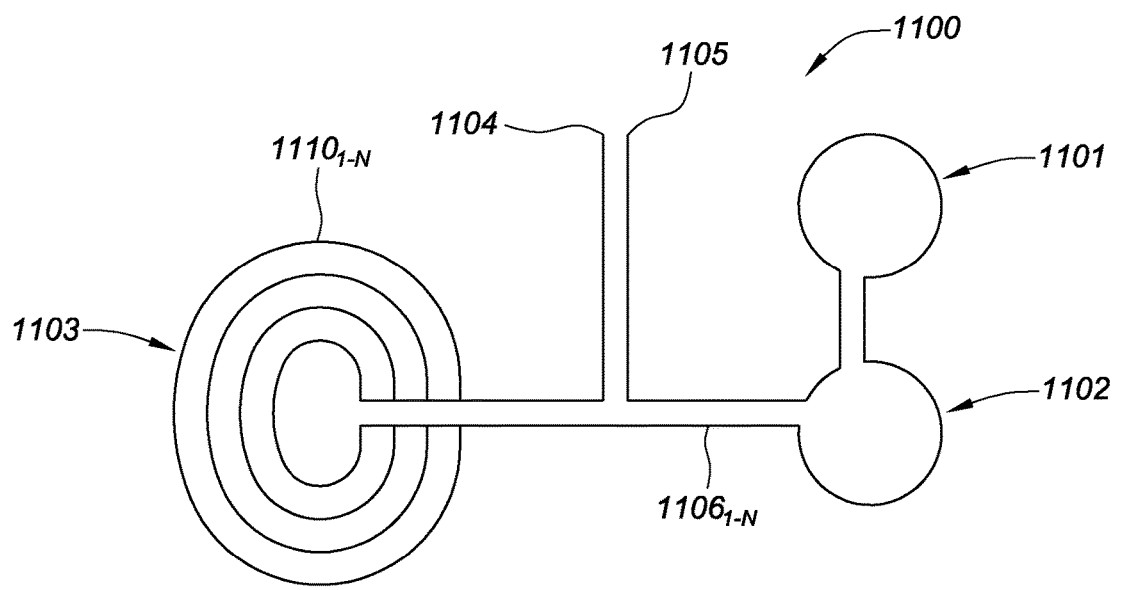
FIG. 11 is a diagrammatic view of a magnetic field transmitter, consistent with various aspects of the present disclosure.
Figure 12:
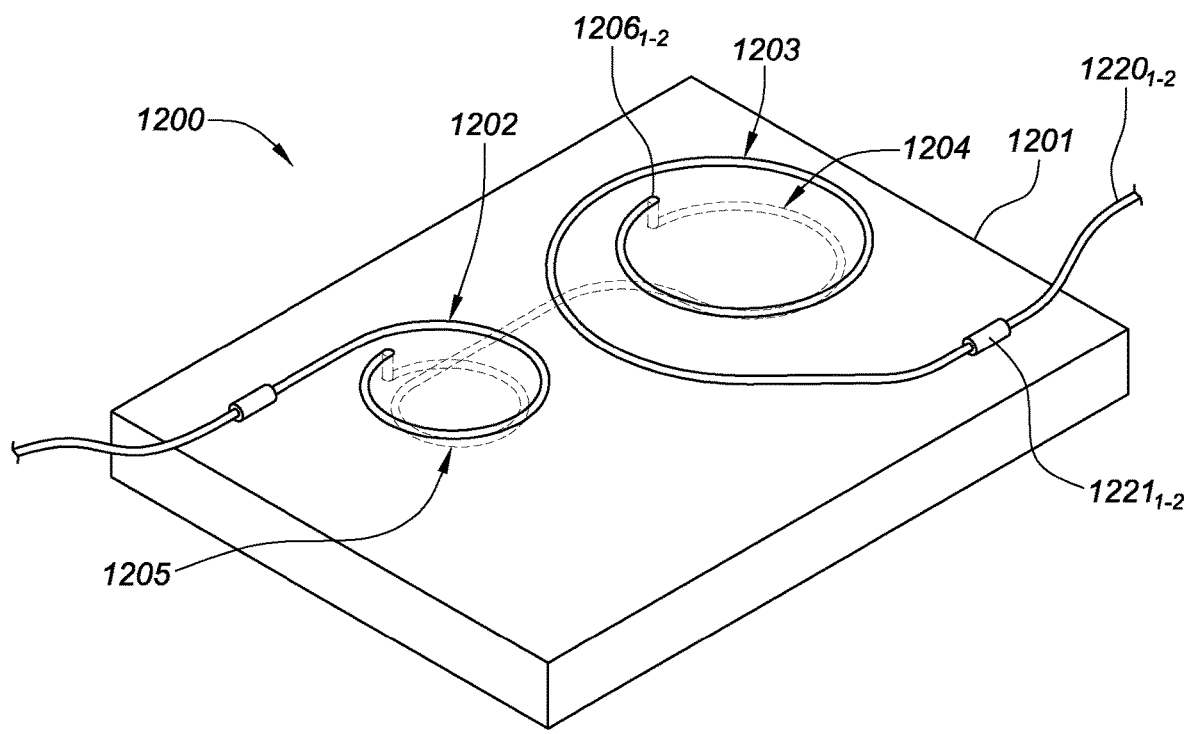
FIG. 12 is an isometric side-view of a magnetic field transmitter with hidden lines shown, consistent with various aspects of the present disclosure.

It is to be further understood that Applicant has not only contemplated magnetic field transmitters in accordance with the figures presented above, but combinations thereof and as further presented, for example, in FIGS. 11-12.

FIG. 11 is a diagrammatic view of a magnetic field transmitter 1100, consistent with various aspects of the present disclosure. The magnetic field transmitter includes three coils 1101, 1102, and 1103 which are coupled to one another via intermediate traces/wires $1106_{1-N}$, and are co-planar relative to one another. In the present embodiment, each of the coils are arranged in series and with the same winding direction. When a voltage is applied across input/outputs 1104 and 1105, the three coils produce an amplified magnetic field of a single polarity.

A first coil 1103 of magnetic field transmitter 1100 includes one or more windings $1110_{1-N}$ which may be driven by a current to produce a magnetic field that extends through a center point of the first coil. Each of the windings $1110_{1-N}$ are placed in parallel relative to one another, and extend circumferentially about the center point of the first coil. Each of the individual coils amplify the resulting magnetic field. By utilizing concentric coils in a single plane, a z-depth of the transmitter may be minimized. Moreover, as the plurality of coils $1110_{1-N}$ of the present embodiment are placed in parallel to one another, as opposed to in series, damage to one or more of the coils within the transmitter will not result in the failure of the transmitter. The first coil also has reduced resistance characteristics.

FIG. 12 depicts an isometric side-view of a magnetic field transmitter 1200 with hidden lines shown, consistent with various aspects of the present disclosure. The magnetic field transmitter 1200 includes a multi-layer substrate 1201. The multi-layer substrate may be compatible with known printed circuit board ("PCB") manufacturing techniques. Electrical traces may be printed on a first layer of the PCB substrate to form first and second windings, 1202 and 1203, respectively. The end of each of the first and second windings are electrically coupled to vias $1206_{1-2}$ which extend between the first and a second layer of the PCB substrate and couple the first and second windings to third and fourth windings, 1204 and 1205, respectively. The third and fourth windings may also be formed of electrical traces printed to a second layer of the PCB substrate.

In the present embodiment, the first winding 1202 and the fourth winding 1205 have a first winding direction, and the second winding 1203 and third winding 1204 have a second winding direction, opposite the first winding direction. As a result, the fourth winding amplifies a first magnetic field emitted by the first winding, and the third winding amplifies a second magnetic field of the second winding. The first and second magnetic fields having opposing fields that create a rapidly-decaying magnetic field.

The magnetic field transmitter 1200 may be coupled to lead wires $1220_{1-2}$ at solder pads $1221_{1-2}$. The lead wires may be electrically coupled to a power source and/or controller circuitry, for example.

When exposed in an x-ray image frame, where the x-ray source and x-ray detector are aligned with a top and bottom surface of magnetic field transmitter 1200, vias $1206_{1-2}$ are the most x-ray visible aspect of the transmitter. However, such x-ray visibility may be further reduced using one or more of the teachings discussed in reference to FIGS. 6A-7B. As the coils formed on the first and second layers of the substrate are of varying diameter (and/or center-points), the coils exhibit reduced x-ray visibility. The coils may further have a reduced thickness and extended width to further facility x-ray translucency.

It is to be understood that various other configurations and quantities of transmitter coil arrays are considered and readily implemented in view of the present disclosure. In this way, based on a given application (or magnetic field demand), additional coils may be added to an array or alternatively more complex coils to produce higher magnetic moments, such as by adding additional windings or winding shapes with improved efficiencies.

In at least one embodiment, the coils of the transmitters may be thin and flat, such that they can be easily integrated into or associated with an operating table. Relatively thin and flat transmitters facilitate x-ray transparency of the transmitter. The transmitters may also be integrated into flexible circuitry. In an embodiment, the height of each transmitter can typically range from about 10 micrometers to about 0.25 millimeters. Thus, the transmitters may be thin and substantially flat, facilitating placement of the transmitters under a mattress or operating table.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In various embodiments of the present disclosure, a magnetic field transmitting element may include two or more partial winds which extend across a common plane. Each of the partial winds are electrically parallel to one another, and extend circumferentially about a common center point.

What is claimed is:

1. An apparatus for generating a magnetic field for tracking of an object within an area of interest, the apparatus comprising:
a magnetic field transmitting element configured and arranged to emit the magnetic field in the area of interest, the magnetic field transmitting element being x-ray translucent,
wherein the magnetic field transmitting element includes a multi-layer substrate having a first layer with first electrical traces disposed on a top outermost surface of the multi-layer substrate and a second layer with second electrical traces disposed on a bottom outermost surface of the multi-layer substrate, wherein first and second electrical traces being electronically coupled to one another with vias, which extend through the substrate between the first and second layers, the first and second electrical traces and the vias forming a coil electrically coupled to a power source, the coil configured to generate the magnetic field.

2. The apparatus of claim 1, wherein the apparatus includes two or more magnetic field transmitting elements configured and arranged to operate in a complimentary polarity which amplifies a magnetic field strength of the magnetic field, or in an opposing polarity to cause the magnetic field to rapidly-decay.

3. The apparatus of claim 2, wherein the two or more magnetic field transmitting elements are electrically coupled in series.

4. The apparatus of claim 1, wherein:
the magnetic field transmitting element is further configured and arranged to be attached to a patient examination table; and
the area of interest is located above the patient examination table.

5. The apparatus of claim 1, wherein the magnetic field transmitting element is further configured and arranged to be placed on a chest of a patient, and the area of interest is a cardiac muscle.

6. The apparatus of claim 1, wherein the magnetic field transmitting element is further configured and arranged to be coupled to a patient examination table, the area of interest is a cardiac muscle, and the tracked object is an intravascular catheter.

7. An apparatus for generating a magnetic field for tracking of an object within an area of interest, the apparatus comprising:

a magnetic field transmitting element configured and arranged to emit the magnetic field in the area of interest, the magnetic field transmitting element being x-ray translucent, wherein the magnetic field transmitting element includes a multi-layer substrate having a first layer with first electrical traces disposed on a top outermost surface of the multi-layer substrate and a second layer with second electrical traces disposed on a bottom outermost surface of the multi-layer substrate, the substrate includes one or more rounded edges configured and arranged to facilitate winding of the first and second electrical traces about the substrate to reduce a signature of the magnetic field transmitting element on an x-ray image, wherein the first and second electrical traces form a coil electrically coupled to a power source, the coil configured to generate the magnetic field.

* * * * *